(12) United States Patent
Spinelli et al.

(10) Patent No.: US 8,269,950 B2
(45) Date of Patent: Sep. 18, 2012

(54) ELASTIC BACKSCATTERING AND BACKREFLECTION LIDAR DEVICE FOR THE CHARACTERIZATION OF ATMOSPHERIC PARTICLES

(75) Inventors: Nicola Spinelli, Naples (IT); Xuan Wang, Sant' Arpino (IT); Maria Grazia Frontoso, Pollena Trocchia (IT)

(73) Assignees: Consiglio Nazionale Delle Ricerche-INFM Istituto Nazionale per la Fisica Della Materia, Genoa (IT); Cnism-Consorzio Nazionale Interuniversitario per le Scienze Fisiche Della Materia, Rome (IT)

(*) Notice: Subject to any disclaimer, the term of this patent is extended or adjusted under 35 U.S.C. 154(b) by 327 days.

(21) Appl. No.: 12/498,100

(22) Filed: Jul. 6, 2009

(65) Prior Publication Data

US 2010/0026981 A1 Feb. 4, 2010

(30) Foreign Application Priority Data

Jul. 7, 2008 (IT) ................ TO2008A0519

(51) Int. Cl.
*G01C 3/08* (2006.01)
*G01N 21/00* (2006.01)

(52) U.S. Cl. ........................ 356/4.01; 356/342

(58) Field of Classification Search ............... 356/4.01, 356/337, 28–28.5, 342
See application file for complete search history.

(56) References Cited

U.S. PATENT DOCUMENTS

| | | | | |
|---|---|---|---|---|
| 5,255,065 A * | 10/1993 | Schwemmer | ............... | 356/4.01 |
| 5,598,263 A * | 1/1997 | Safa | ............... | 356/342 |
| 5,663,710 A | 9/1997 | Fasig et al. | | |
| 5,847,815 A * | 12/1998 | Albouy et al. | ............... | 356/4.01 |
| 6,281,969 B1 | 8/2001 | Gelbwachs | | |
| 6,384,903 B1 * | 5/2002 | Fuller | ............... | 356/4.01 |
| 6,535,158 B2 * | 3/2003 | Wilkerson et al. | ............... | 342/26 D |
| 6,650,402 B2 * | 11/2003 | Sullivan et al. | ............... | 356/4.01 |
| 6,717,655 B2 * | 4/2004 | Cheng et al. | ............... | 356/4.01 |
| 7,064,817 B1 * | 6/2006 | Schmitt et al. | ............... | 356/139.03 |
| 7,583,364 B1 * | 9/2009 | Mayor et al. | ............... | 356/4.01 |
| 2002/0075472 A1 * | 6/2002 | Holton | ............... | 356/4.01 |
| 2008/0137058 A1 * | 6/2008 | Cesare | ............... | 356/4.01 |

OTHER PUBLICATIONS

Nubo Sugimoto, Coninous Lidar Observations and Aerosols and Clouds in Tsukuba, Japan and Jakarta Indeonesia, TuC2 (Invited)/ CLEO/Pacific Rim 99/ pp. 29-30.*
Nubo Sugimoto, Continous Lidar Observations and Aerosols and Clouds in Tsukuba, Japan and Jakarta Indeonsesia, TuCd (invited)/ CEO, Pacific Rom 99/ pp. 29-30 (1999).*

(Continued)

*Primary Examiner* — Isam Alsomiri
*Assistant Examiner* — Antoine J Bedard
(74) *Attorney, Agent, or Firm* — Sughrue Mion, PLLC (57) ABSTRACT

A method is described for the characterization of atmospheric particles by means of a lidar device. The method provides to send a laser pulse in the atmosphere, a part of which is directly backscattered by the particles in the atmosphere. A reflecting optical device is provided, that is positioned at a predetermined distance d from the lidar device, whereby a part of the laser pulse that directly reaches the reflecting device is back-reflected and is later backscattered by the particles in the atmosphere thus generating a counterpropagating backscattering signal directed towards the reflecting device, which signal reaches the reflecting device and is backreflected towards the lidar device. The lidar device detects the direct backscattering and counterpropagating signals. The optical characteristics of the particles are determined on the basis of the direct backscattering signal and the counterpropagating backscattering signal.

6 Claims, 5 Drawing Sheets

OTHER PUBLICATIONS

James D. Klett, "Stable analytical inversion solution for processing lidar returns", Applied Optics, 1981, pp. 221-220, vol. 20, No. 2.

Frederick G. Fernald et al., "Determination of Aerosol Height Distribution by Lidar", Journal of Applied Meterology, 1971, pp. 482-489, vol. 11.

Albert Ansmann et al., "Measurement of atmospheric aerosol extinction profiles with a Raman lidar", Optics Letters, 1990, pp. 746-748, vol. 15, No. 13.

Christine Bockmann, "Hybrid regularization method for the ill-posed inversion of multiwavelength lidar data in the retrieval of aerosol size distributions", Applied Optics, 2001, pp. 1329-1342, vol. 40, No. 9.

Michael Sicard et al., "Variational method for the retrieval of the optical thickness and the backscatter coefficient from multiangle lidar profiles", Applied Optics, 2002, pp. 493-502, vol. 41, No. 3.

Xuan Wang et al., Retrieval of atmospheric particles optical properties by combining ground-based and spaceborne lidar elastic scattering profiles, Optics Express, 2007, pp. 6734-6743, vol. 15, No. 11.

X. Wang et al., "An Algorithm to determine cirrus properties from analysis of multiple-scattering influence on lidar signals", Applied Physics B, 2004, pp. 1-7.

A. Ansmann et al., Combined Raman Elastic-Backscatter LIDAR for Vertical Profiling of Moisture, Aersol Extinction, Backscatter, and LIDAR Ratio, Applied Physics B, 1992, pp. 18-28.

Detlef Muller et al., "Micophysical particle parameters from extinction and backscatter lidar data by inversion with regularization: simulation", Applied Optics, 1999, pp. 2358-2368, vol. 38, No. 12.

Shane D. Mayor et al., "Raman-shifted eye-safe aerosol lidar", Applied Optics, 2004, pp. 3915-3924, vol. 43, No. 19.

* cited by examiner

ELASTIC BACKSCATTERING AND BACKREFLECTION LIDAR DEVICE FOR THE CHARACTERIZATION OF ATMOSPHERIC PARTICLES

FIELD OF THE INVENTION

The present invention relates to a method for the characterization of atmospheric particles by means of a lidar device, comprising the following steps:
sending a laser pulse in the atmosphere, part of which is backscattered by the particles in the atmosphere thus generating a direct backscattering signal that propagates towards the lidar device;
detecting the direct backscattering signal; and
determining optical characteristics of the particles on the basis of the detected direct backscattering signal.

PRIOR ART

The application of the lidar technique to the characterization of the atmospheric aerosols is well established. It is implemented according to several forms, by exploiting different physical phenomena and different technologies. However, it is highly limited by some general constraints, particularly concerning the actual use in the air quality control in the public and private fields, such as, for example, the control of fine particles in urban areas, the control of emissions of industrial plants, energy production plants, incinerators, etc.

The underlying principle is as follows: a short-duration laser pulse (typically from some units to one hundred nanoseconds ($10^{-9}$ s)) is sent to the atmosphere, and the backscattered radiation is collected by a reception and acquisition system (telescope, spectral selection system, detectors). The backscattered radiation transports information on the thickness of the air it passes through, while the detection time allows determining the distance between atmospheric layers.

In the simplest configuration, a lidar for particles uses only one laser beam and only one detecting system tuned at the same wavelength of the laser. In such configuration, the physical process involved is that of the elastic backscattering by the gases and the atmospheric particles.

In this case, the equation describing the revealed signal as a function of the distance from the apparatus contains, as the unknowns, the extinction coefficient $\alpha_p(z, \lambda)$ and the backscattering coefficient $\beta_p(z, \lambda)$ of the particles, which constitute the optical parameters to be determined (z represents the distance of the air layer under consideration, and $\lambda$ the used wavelength).

Actually, even supposing all the instrumental parameters as known, the lidar equation cannot be exactly solved in the unknowns $\alpha_p(z, \lambda)$ and $\beta_p(z, \lambda)$. For this reason, when other data are not available, it is necessary to assume some hypotheses that directly regard the nature of the particles. The method typically used in this case consists in considering the value of the ratio between the extinction coefficient and the backscattering coefficient, called Lidar Ratio (LR), as known, and in applying one of the known algorithms [1, 2].

The selection of the LR value is done starting by knowing the atmospheric conditions, by statistical analyses, classifications of the particles according to the sites, conditions, seasons, relative humidity, etc. Then it shall be apparent how such selection involves enormous uncertainty, generally estimated as being between 10% and 50%, about the backscattering coefficient. The uncertainty about the extinction coefficient is obviously even higher; therefore, the arbitrariness extent in characterizing the particles often becomes unacceptable.

The difficulty is overcome by providing the lidar system with the possibility to simultaneously detect also the optical signal corresponding to the Raman diffusion by the nitrogen or oxygen molecules (in both cases, they are stable constituents of the atmosphere, the concentration of which as a function of the altitude can be considered as known with a good accuracy).

The simultaneous detection of the elastic signal and the Raman signal allows the application of known algorithms for the determination of both the extinction coefficient and the backscattering coefficient at the wavelength of the used laser beam [3, 4], though with some hypothesis on particular aspects, such as the dependence of the extinction coefficient upon the wavelength, which, however, can be quantitatively controlled.

On the other hand, the Raman technique cannot be applied to the near-infrared wavelengths, due to the dependence of the cross section of the process from $\lambda^{-4}$. Furthermore, the low absolute value of the Raman cross section involves the use of high-power laser beams, with resulting economical, technical and safety problems which add up to a not negligible complexity of data processing.

Furthermore, the determination of the particles chemical/physical parameters is possible through the application of inversion algorithms only if measures of $\alpha_p$ and $\beta_p$ are available at different wavelengths [5, 6], particularly also in the infrared, where, however, the Raman technique cannot be applied.

A different technique for the determination of atmospheric particles optical parameters provides for the provision of the lidar apparatus with an angular scan system, so that the atmosphere is monitored in a short time interval along different directions, which form known angles relative to the zenith direction [7]. In the hypothesis that the atmosphere remains stable when carrying out the measurements, and especially that the properties of the atmosphere itself depend only on the vertical coordinate (horizontal homogeneity), this technique allows to directly obtain the measurement of the particles optical thickness and the backscattering coefficient as a function of the vertical coordinate.

While the technical complication relative to the handling of the lidar can be overcome, the horizontal homogeneity conditions of the atmosphere apply only in special cases, in which the weather conditions and the site orography are particularly favourable. On the whole, the applicability of this method is really limited.

Other variants of the lidar technique are used in some cases (high spectral resolution lidar, differential absorption lidar); however, they are based on an intensive spectral analysis of the signal, require specific laser sources (narrow line in the first case, tunable double wavelength in the second one), and the knowledge of the nature of the target material. The application referred above is further limited also by the fact that the absorption by the particles predominantly occurs in the ultraviolet ($\lambda$<300 nm) and on a broad band, resulting in difficulties related to the interference with gaseous components and the need to have tunable laser sources.

With the aim to overcome the above-mentioned drawbacks, the inventors [8] have recently introduced a new processing technique of the signals of two lidar apparatuses which probe the atmosphere collinearly, but in different directions, as happens for ground, satellite, or airplane-based lidars (CESC—Counterpropagating Elastic Signal Combination).

With that technique, it is possible to use only the elastic backscattering to obtain a direct measurement of the aerosol backscattering coefficient at any wavelength without any hypothesis on the particles chemical/physical characteristics. The technique allows independently determining also the optical thickness and the aerosol extinction coefficient, under favourable signal-to-noise ratio conditions.

However, the above-mentioned technique has the drawback of being able to be applied only by simultaneously operating with two lidar devices that are positioned at the extremities of the atmosphere length being controlled, and pointing one towards the other. Therefore, it provides the duplication of the lidar apparatus, with consequences on costs, logistics, and complexity in overall system management.

SUMMARY OF THE INVENTION

The present invention has as its object to allow an accurate determination of the optical parameters and spatial distribution, without turning to a priori hypotheses, thus avoiding the drawbacks of the prior art.

According to the present invention, that object is achieved by a method for the characterization of atmospheric particles of the type defined at the beginning, in which
- a reflecting optical device is provided, which is positioned at a predetermined distance from the lidar device, whereby a part of the laser pulse which directly reaches the reflecting device is backreflected and then backscattered by the particles in the atmosphere thus generating a counterpropagating backscattering signal directed towards the reflecting device, which signal reaches the reflecting device and is itself backreflected towards the lidar system; and
- also the counterpropagating backscattering signal is detected, whereby said determination of the particles characteristics occurs also on the basis of the detected counterpropagating backscattering signal.

Particular embodiments of the invention are the subject of the dependant claims.

It is a further subject of the invention a lidar system for the characterization of atmospheric particles by means of a method according to the invention, which includes:
- a lidar device, comprising a transmitting system adapted to send said laser pulse in the atmosphere, and a receiver system adapted to detect said direct backscattering and counterpropagating signals; and
- a reflecting optical device positioned at a predetermined distance from the lidar device, adapted to reflect to the lidar device the part of the laser pulse that directly reaches the reflecting device and the counterpropagating backscattering signal.

In brief, the present invention is based on the application of a backreflection technique for the generation of counterpropagating lidar signals. This technique allows implementing devices which use only the elastic backscattering and provide a direct measurement of the aerosol backscattering coefficient at any wavelength, without any hypothesis on the chemical-physical characteristics of the particles (thanks to an adaptation of the above-mentioned CESC algorithm). The technique allows independently determining also the optical thickness and the aerosol extinction coefficient, under favourable signal-to-noise ratio conditions.

The application can provide the simultaneous employment of different wavelengths (from the ultraviolet to the infrared); in this manner, a complete characterization of the particles and the time-space distribution of the chemical-physical properties thereof, such as the concentration, refraction index, composition, and size distribution is possible.

BRIEF DESCRIPTION OF THE DRAWINGS

Further characteristics and advantages of the invention will be set forth in more detail in the following detailed description of an embodiment thereof, given as a non-limiting example, with reference to the annexed drawings, in which.

DESCRIPTION OF A PREFERRED EMBODIMENT OF THE INVENTION

Figure 1:
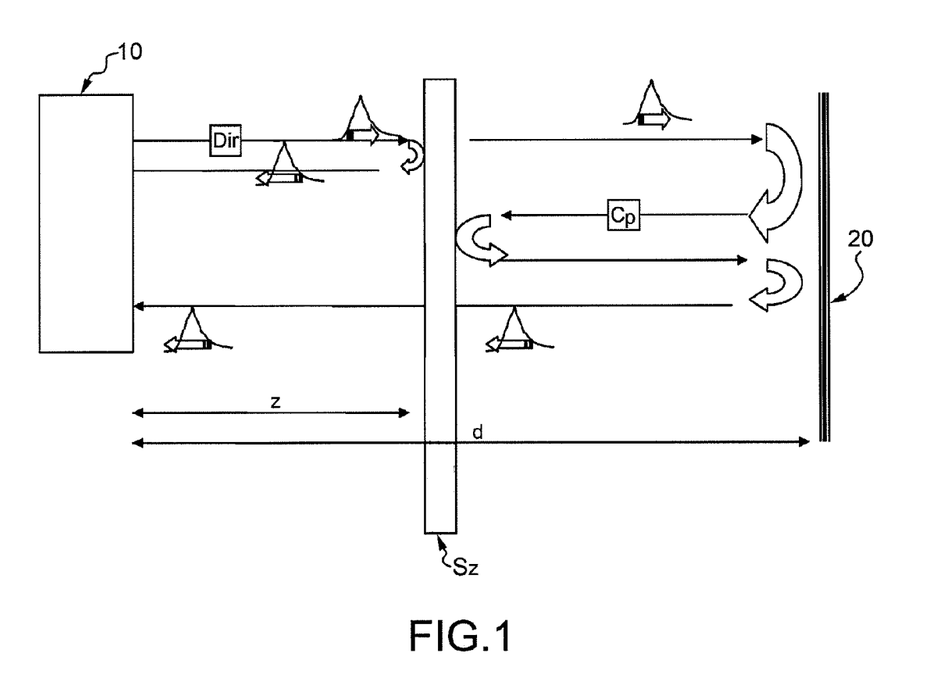
FIG. 1 is a schematic representation of a method for the characterization of atmospheric particles according to the invention.

With reference to FIG. 1, a method for the characterization of atmospheric particles provides for the use of a lidar device 10, which conventionally sends a laser pulse in the atmosphere, part of which signal is conventionally backscattered by the particles in the atmosphere thus generating a backscattering signal, which in the present description will be referred to as "direct", that propagates to the lidar device 10. The laser pulse path which partially interacts with the particles, thus generating the direct backscattering signal, is indicated with Dir in FIG. 1.

The proposed method according to the invention is based on the idea to place a reflecting optical device 20, such as a mirror, on the laser beam path, at a predetermined distance d from the lidar device 10. In this manner, a part of the laser pulse that directly reaches (i.e, without interacting with the particles) the reflecting device 20 is backreflected by said device, and subsequently is backscattered by the particles in the atmosphere thus generating a further backscattering signal, which will be referred to in the present description as "counterpropagating", directed towards the reflecting optical device 20. The counterpropagating backscattering signal reaches the reflecting device 20 and is backreflected towards the lidar device 10, where it will be detected. The laser pulse path that partially reaches the reflecting device and is backreflected by it, and subsequently interacts with the particles, thus producing the counterpropagating backscattering signal, is indicated with Cp in FIG. 1.

According to the invention, the lidar 10 itself will be able to detect both the signal corresponding to the passage through the atmospheric thickness in the direction from the lidar device to the mirror, and that corresponding to the inverse path.

The situation is schematized in FIG. 1; for the sake of simplicity, the atmosphere probed by the laser beam is supposed as being of null density (i.e., negligible) everywhere but in a thin layer Sz, positioned at a distance z from the lidar device 10.

The signal which is backscattered by the atmospheric layer reaches the lidar device 10 receiving system by following both the Dir path (normal lidar signal) and the Cp path (counterpropagating lidar signal), after a period of time that will be respectively equal to $$t_1 = \frac{2 \cdot z}{c}; t_2 = 2 \cdot \frac{(d + (d - z))}{c}.$$

In practice, the received signal will have 3 components: a pulse corresponding to the direct backdiffusion by the layer, at time $t_1$, a signal due to the direct reflection of the mirror (relative to the part of the laser pulse which has not been subjected to any interactions with the particles) at time $$t_m = \frac{2 \cdot d}{c},$$

and that due to the backdiffusion of the counterpropagating radiation at time $t_2$. It shall be apparent that the relationship: $t_m - t_1 = t_2 - t_m$ applies, which expresses the symmetry property introduced by the plane mirror.

The two (direct backscattered and counterpropagating) lidar signals are temporally separated on the lidar system 10 detector, therefore they can be used for the application of an algorithm derived from the above-mentioned CESC algorithm.

Let us consider the backscattered signal as having the same wavelength of the incident laser beam (elastic backscattering signal). Hereinafter, the signals expressed in terms of photon number, corrected by the square of the path from the lidar device (this correction compensates for the variation in the receiver acceptance solid angle), respectively corresponding to the direct backdiffusion of the layer Sz and to the backdiffusion of the of the counterpropagating signal, will be indicated with $RCS_D(z)$ and $RCS_C(z)$.

The two signals can be written as:

$$RCS_C(z) = r^2 \cdot \frac{E_0}{h\upsilon} \cdot A \cdot \Delta z \cdot \eta \cdot O'(z) \cdot \beta(z) \cdot \exp(-2\tau_{0M}) \cdot \exp(-2\tau_{zM}) \quad (1)$$

$$RCS_D(z) = \frac{E_0}{h\upsilon} \cdot \Delta z \cdot A \cdot \eta \cdot O(z) \cdot \beta(z) \cdot \exp(-2\tau_{0z}) \quad (2)$$

In the equations 1) and 2), z indicates the distance from the lidar, $E_0$ is the energy of the signal which is emitted by the laser, h is the Planck's constant, u is the radiation frequency, A is the receiving telescope useful surface, $\Delta z$ is the spatial resolution, $\eta$ is the apparatus overall efficiency, r is the mirror reflectivity, $\beta(z)$ is the total backscattering coefficient, and O(z) and O'(z) are the lidar overlap functions.

The terms $$\tau_{0M} = \int_o^d \alpha(\zeta)d\zeta, \tau_{zM} = \int_z^d \alpha(\zeta)d\zeta \text{ and } \tau_{0z} = \int_o^z \alpha(\zeta)d\zeta$$

respectively represent the optical thickness along the path from the lidar 10 to the mirror 20, along the path from the mirror 20 to the layer Sz at a distance z from the lidar 10, and along the path from the lidar 10 to the layer Sz at a distance z, while $\alpha(\zeta)$ is the extinction coefficient as a function of the spatial coordinate.

Let us restrict for the moment the analysis to the observation of atmospheric layers placed at a higher distance than the total overlap height. In this case, it is possible to consider the functions O(z) and O'(z) as constant, and to include the value thereof in the instrumental constant.

The product of the two signals will be given by:

$$P(z) = RCS_C(z) \cdot RCS_D(z) \quad (3)$$

$$= \left(\frac{E_0}{h\upsilon}\right)^2 \cdot r^2 \cdot (A \cdot \Delta z)^2 \cdot \eta^2 \cdot \beta^2 \cdot (z) \cdot$$
$$\exp[-2 \cdot (\tau_{0M} + \tau_{zM} + \tau_{0z})]$$

The relationship: $\tau_{0z} + \tau_{zM} = \tau_{0M}$ applies, and therefore the backscattering coefficient can be obtained from the equation (3) as:

$$\beta(z) = \sqrt{P(z)} \cdot \frac{h\upsilon}{E_0 \cdot A \cdot \Delta z \cdot T_{0M}^2 \cdot r \cdot \eta} \quad (4)$$

In equation (4) the quantity $T_{0M} = \exp(-\tau_{0M})$ indicates the atmospheric transmissivity between the lidar and the mirror position. The value of $T_{0M}$ can be determined by a calibration procedure of the apparatus, which consists in measuring the width of the optical signal which is reflected directly by the mirror surface. In fact, this signal can be expressed as:

$$S_M = \frac{E_0}{h \cdot \upsilon} \cdot r \cdot \eta \cdot T_{0M}^2 \cdot \frac{A}{s}$$

where s is the laser beam cross-section surface after the going and return path.

Therefore, the total backscattering coefficient becomes:

$$\beta(z) = \frac{1}{S_M \cdot \Delta z \cdot s} \sqrt{P(z)}$$

and the backscattering coefficient of the particles can be obtained from the relationship:

$$\beta_p(z) = \beta(z) - \beta_{mol}(z)$$

in which $\beta_{mol}(z)$ represents the contribution of the molecular component, which can be determined starting from standard atmospheric models and by knowing temperature and pressure.

If the ratio R of the equations (1) and (2) is taken into account:

$$R(z) = \frac{RCS_C(z)}{RCS_D(z)} \quad (7)$$
$$= r^2 \cdot \exp[-2(\tau_{0M} + \tau_{zM} - \tau_{0z})]$$
$$= r^2 \cdot \exp(-4\tau_{0M}) \cdot \exp(-4\tau_{0z})$$

The optical thickness to the distance z will be obtained from:

$$\tau_{0z}(z) = \frac{1}{4}\left[\ln\frac{R(z)}{r^2} + 4\tau_{0M}\right] \quad (8)$$

The optical thickness between to points of coordinates $z_{min}$ and $z_{max}$ is then:

$$\tau(z_{max} - z_{min}) = \frac{1}{4}[\ln R(z_{max}) - \ln R(z_{min})] \quad (9)$$

The extinction coefficient of the particles $\alpha_p(z)$ is therefore evaluated by deriving the equation (7) with respect to z:

$$\alpha_p(z) = \frac{1}{4}\frac{d}{dz}[\ln R(z)] - \alpha_{mol}(z) \quad (10)$$

Finally, it has to be remarked that the only hypothesis which has to be verified is that the multiple scattering contribution can be neglected. The multiple scattering influence depends on the optical thickness of the probed atmospheric layer and the solid angle under which it is observed. Unfavourable conditions occur in the presence of clouds and in dense fog conditions.

Figure 2:
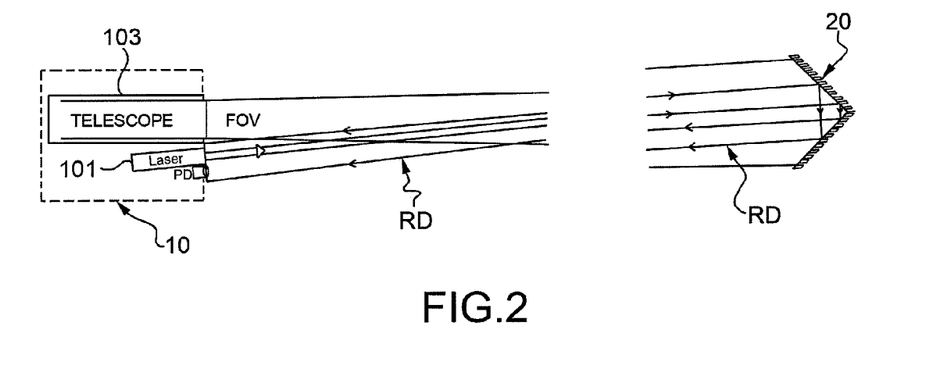
FIG. 2 is a schematic representation of a lidar system for carrying out the method of FIG. 1.

The system requires a calibration which can be carried out, as indicated above, by detecting the signal directly reflected by the mirror 20. This method has the advantage of being applicable during each measurement run. The optical signal corresponding to the direct reflection of the mirror 20 is of a very high intensity, while the lidar signal, and particularly the counterpropagating one, is very weak, therefore the simultaneous detection of the two signals by the same detector would require very high dynamics of the detector and the acquisition system. This difficulty can be overcome: 1) by using a separate detector (for example, a fast photodiode) for the radiation which is reflected by the mirror, and 2) with an appropriate arrangement of the laser and the receiving apparatus (bistatic configuration).

In practice, it is necessary to make so that the beam propagation direction and the pointing direction of the receiving telescope form a small angle, sufficient to make so that the radiation which is directly reflected by the mirror impinges on the photodiode, but won't enter in the telescope field of view.

The situation is schematized in FIG. 2, where the laser system is indicated with 101, the receiving telescope is indicated with 103, while the separate detector for the radiation reflected by the mirror 20 is indicated with PD.

The configuration can be implemented in the practice, provided that the laser beam divergence is significantly lower than the opening of the telescope field of view FOV, but this condition is always verified in the practice.

In this configuration, the photodiode PD detects the direct reflection signal, which is indicated RD in FIG. 2, while the telescope 103 collects the radiation which is backscattered by the particles.

It has to be considered the fact that this configuration implies that the laser beam and the telescope field of view are not completely overlapped; therefore, at small distances the overlap function O(z) indicated in the equation (2) has to be considered. In particular, this function assumes different values for the direct backscattered signal and the counterpropagating one. In both cases, it depends only on the device geometrical parameters, therefore it is a characteristic which, once it has been determined, is modified only when the apparatus undergoes some variations. It follows that it can be determined during the testing step by using two similar devices which are arranged so that the partial overlap region of one of them corresponds to the total overlap region of the other one.

A different calibration methodology consists in placing a device for the determination of the particles concentration along the laser beam path, at a known distance from the lidar. A nephelometer can allow determining the backscattering coefficient in the considered point, therefore using a similar procedure to the previously described one. The frequency with which this type of calibration has to be repeated depends on the lidar system characteristics stability (laser energy, detector efficiency); such parameters can be made very stable with the currently available technologies.

Figure 3:
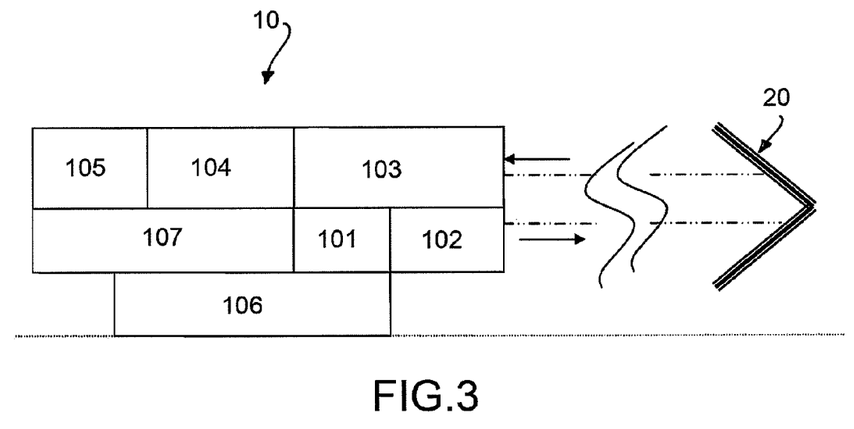
FIG. 3 represents a functional block diagram of the lidar system of FIG. 2.

The functional block diagram of the lidar device 10 is depicted in FIG. 3. The arrangement of such device is per se conventional, and comprises a laser system 101, deviation optics 102, a telescope 103, receiving and spectral selection optics 104, one ore more detectors 105, a pointing system 106, and a control and acquisition electronics 107.

There are several commercial solutions for the laser system 101, at different wavelengths from the IR to the UV. Table 1 shown herein below reports the typical characteristics for a laser operating in the visible region.

The deviation optics 102 is composed of a beam steerer (system of two plane mirrors), with controlled micrometric handling, for the optimal alignment in the beam propagating direction.

The telescope 103 can be implemented in different configurations, but most likely the most efficient one is the Cassegrain configuration, that allows having a reduced length while keeping the other parameters constant.

The receiving and spectral selection optics 104 provides to send the radiation which is collected by the telescope 103 to the spectral selection system, and from the latter to the detectors. The constructive scheme for a device that operates at three wavelengths is reported in FIG. 4.

Figure 4:
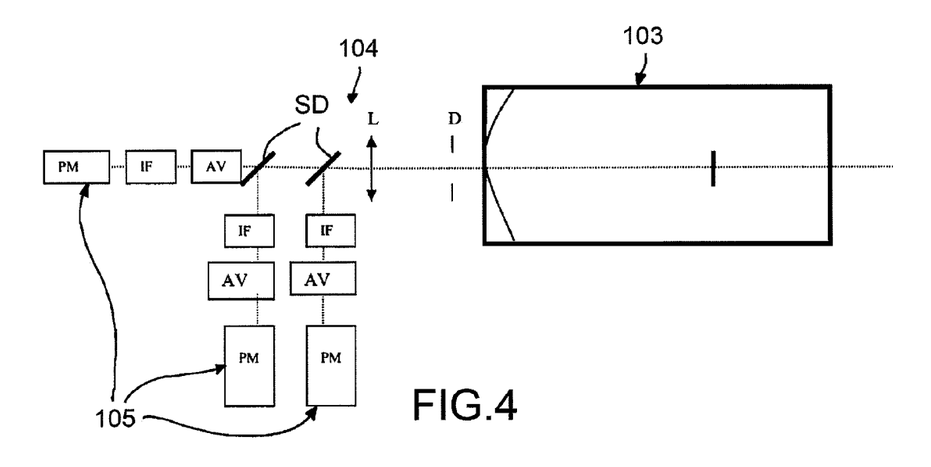
FIG. 4 represents a constructive scheme of a lidar device receiving system operating at three wavelengths.

A diaphragm D positioned in the focal plane of the telescope 103 defines the angular opening of the device. The collected radiation is collimated by a lens L and sent to a system of dichroic mirrors SD and narrow band interferential filters IF, which allow separating the beams corresponding to the different wavelengths.

It can be necessary to vary the intensity of the signals as a function of the measuring conditions (day/night, clouds or fog) in order to maintain the response of the detectors 105 in a linear regime. To this aim, each detecting channel comprises a variable attenuator AV.

A feasible solution for the detectors 105 provides for the use of photomultipliers (indicated with PM in FIG. 4) for the UV or visible radiation, and APD (avalanche photodiode) for the IR radiation.

If the lidar device is used with a series of reflecting elements 20, the pointing system 106 has to orientate it on each of them, in sequence. If only one reflecting element is present, the pointing system 106 can be limited to a manual handling for the alignment with the mirror.

As regards the acquisition and control electronics 107, the functions relate to:
- the control of the device;
- the acquisition of the signals of the detectors, which can take place both in an analog and digital form (photon counting).

The advantages of the system according to the invention are as follows:
- The device allows to directly determine the spatial distribution and the time evolution of the backscattering coefficient, only starting from the elastic signal, without making any a priori hypothesis on the nature of the particles.
- The determination of the backscattering coefficient at different wavelengths results to be not very burdensome both from the technical and the economical point of view compared to the lidar systems utilizing the Raman technique, which in any case cannot be applied in the IR. The proposed device results to be less complex, less expensive, and more manageable than a Raman lidar system.
- The device allows determining with good performance the optical thickness of the probed atmospheric layer and, under favourable signal-to-noise ratio conditions, also the extinction coefficient, and accordingly the Lidar Ratio LR.
- By using different wavelengths, it is possible to determine the Color Index and the Angstrom Coefficient, which express the dependence of the backscattering and the extinction coefficients on the wavelength, respectively.
- The application of the infrared is particularly relevant for the characterization of particles having dimensions ranging between 0.1 mm and 10 mm (PM1, PM2.5, PM10). This results to be particularly useful for an efficient application of the inversion techniques in order to determinate the chemical-physical parameters of the particles (concentration, refraction index, size distribution) for which it is necessary to have measurements of the optical parameters at different wavelengths, which are sufficiently mutually spaced apart.
- It operates with small performance differences in both night and day hours (see simulation described below).
- The implementation for the stand-alone use results to be extremely simple.
- It is self-calibrating, i.e. it re-calibrates during each measurement.

The advantages compared to the conventional measurement systems of the particles relative to the air quality control are:
- the time resolution can be of the order of minutes;
- it is possible to place the lidar apparatus and the mirror at high positions (on poles, buildings, or elevations), so that the radiation path passes through the area to be controlled (high vehicular traffic intensity roads, large particles producing areas, for example, highly industrialized ones, incinerators, energy production plants, etc.);
- by providing the device with a mechanical pointing system, it is possible to obtain a mapping of the particles as a function of time on a large surface.

Simulation

With the purpose to verify the performance of the proposed system, a complete simulation has been carried out.

A typical lidar signal has been simulated, with a spatial resolution of 6 meters. Furthermore, a "noise" component has been introduced, due both to the statistics and the background signal, depending on the electronic noise, the photomultipliers dark current, and the solar radiation.

The wavelength used in the simulation is equal to 532 nm and corresponds to the case in which the background noise is high because of the day light, and furthermore is located in the minimum safety threshold region when using laser beams.

In the simulation, only single-scattering processes by the atmospheric components have been considered, considering the Mie and Rayleigh scatterings by the aerosol particles and the molecules, respectively.

The atmospheric properties have been set by using a standard atmosphere model for the molecular component, and by considering typical urban conditions for the aerosol component. In particular, a situation has been simulated in which the laser beam passes through areas characterized by different contributions in terms of particles, localized in not very large areas, simulating high vehicular traffic intensity roads and large areas, for example, highly industrialized areas.

The distribution of the sources has been selected so as to represent realistic situations and to permit also the determination of the spatial resolution of the final data.

For the sake of simplicity, in the calculation of the atmospheric model spatial profile, the simulation has been carried out by hypothesizing that the system is positioned at sea level and arranged so that the laser beam path is horizontal. Variations from these conditions (lidar positioned at a different altitude and/or arbitrary pointing direction) do not modify the device functionality.

The values of the parameter used in the simulation are listed in the following table 1. They have been obtained by lidar measurements obtained with an apparatus really operating at the same wavelength.

TABLE 1

| Laser | | Telescope | |
|---|---|---|---|
| Energy per pulse (µJ) | 0.5 | Radius (cm) | 15 |
| Repetition frequency (Hz) | 2000 | Focal length (m) | 1 |
| | | Diaphragm opening (mm) | 0.3 |
| Divergence (with Beam Expander) (mrad) | 0.1 | Angular opening (mrad) | 0.3 |
| Wavelength (nm) | 532 | | |
| Pulse duration (ns) | <40 | | |
| Backreflector | | Receiving optics | |
| Distance (m) | 2000 | Overall efficacy | 0.5 |
| Opening (m) | 0.6 | Pass-band interferential filter (nm) | <3 |
| Reflectivity | 0.5 | | |
| Detector | | Band transmissivity | 0.3 |
| Quantum efficiency | 0.3 | Integration time (s) | 600 |
| Spatial resolution (signal) (m) | 10 | Background-day (cps) | 2000 |
| Laser beam - telescope axis distance (cm) | 20 | Background-night (cps) | 0 |

Considered the laser characteristics (energy per pulse, divergence and duration with beam expander), the device fully satisfies the conditions to be complied with according to safety standards when using laser sources [9].

It has been hypothesized that the acquisition of the lidar signal occurs in photon counting, through the use of a commercially available electrical device of the Multiscaler type with a time resolution which is compatible with the spatial resolution of 10 m (dwell time ~70 ns).

For the calculation of the backscattering and the extinction coefficients, the simulated signal has been averaged over 10 minutes. In the processing, no filter has been applied to the signal.

Figure 5:
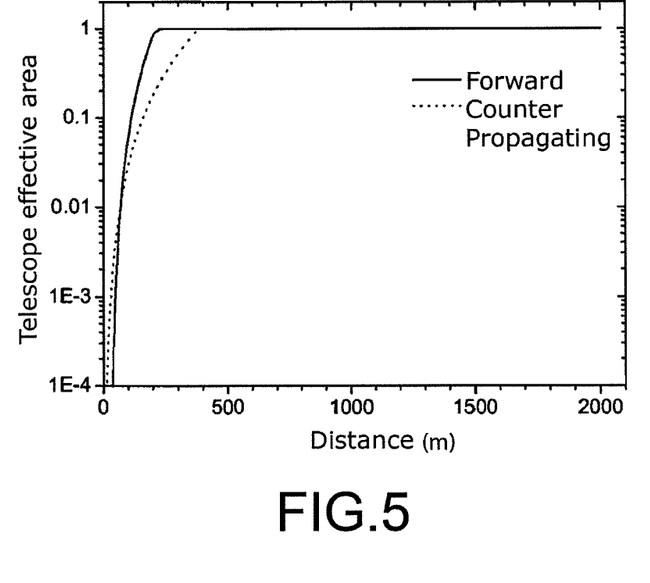
FIG. 5 reports the overlap functions graph for the direct backscattering and the counterpropagating signals.

In FIG. 5, the overlap functions graph is depicted for the direct backscattering and counterpropagating signals. In reconstructing the optical parameters of the particles, these functions are considered as known by means of independent measurements, as previously illustrated.

Figure 6:
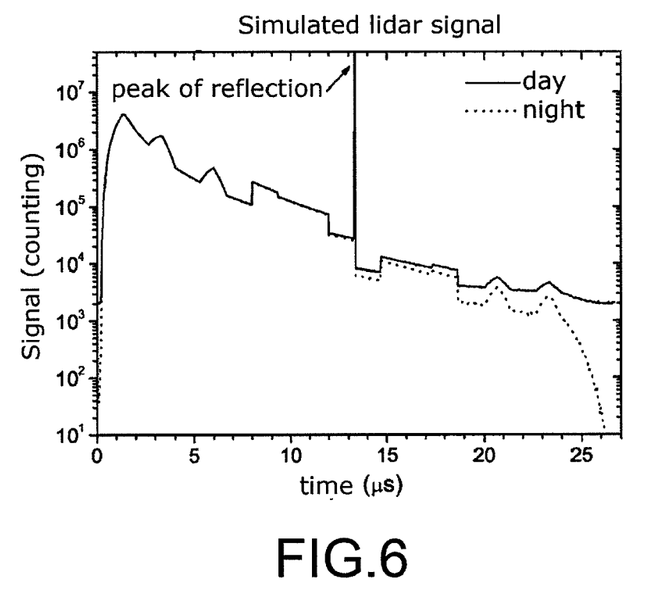
FIG. 6 reports the graph of the lidar signal simulated as a function of time.

In FIG. 6, the simulated signal as a function of time starting from the instant of emission of the laser pulse is depicted.

Figure 7:
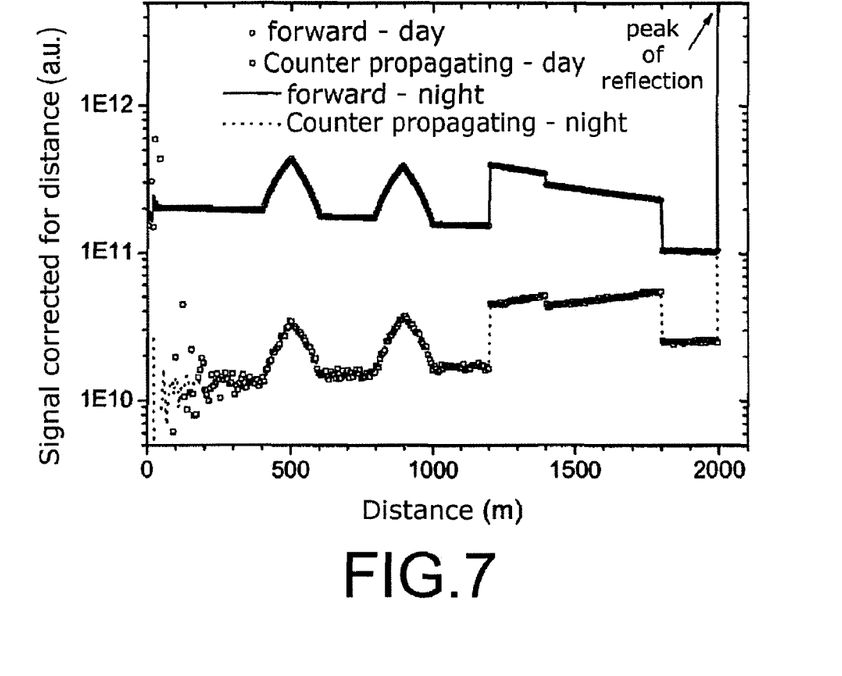
FIG. 7 reports the simulated, range-corrected signal as a function of the distance from the lidar system.

In FIG. 7, the simulated, range-corrected signal is reported as a function of the distance from the lidar device. The upper curve relates to the direct backdiffusion, while the lower one is the result of the backdiffusion of the counterpropagating reflected signal. In order to point out the contribution of the solar light, the simulated signal for both day and night measurements is reported in the Figure.

Figure 8:
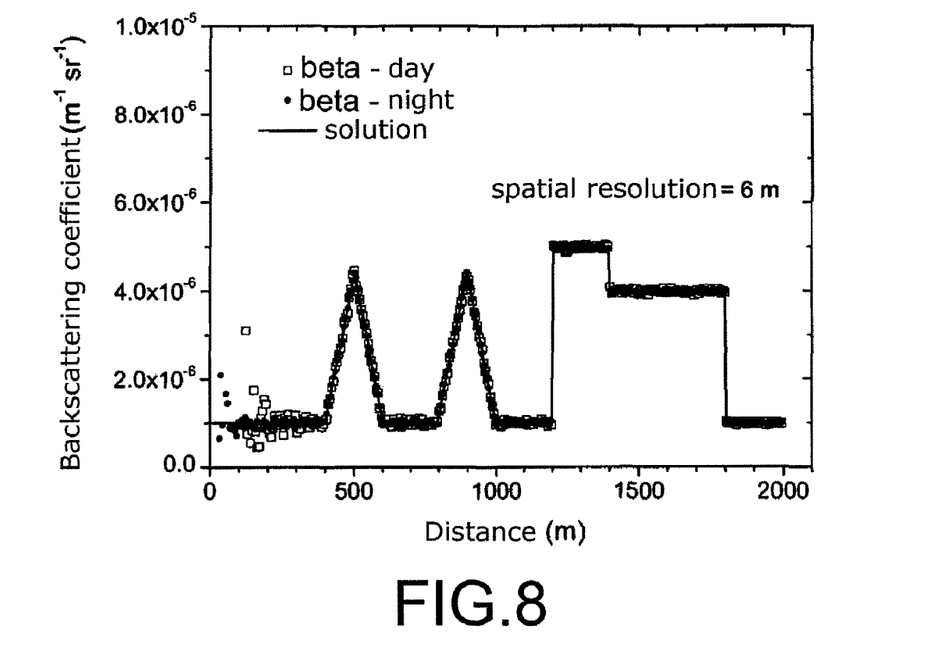
FIG. 8 reports the profile of the aerosol backscattering coefficient determined on the basis of the simulated signal, together with that of the signal assumed by hypothesis in the simulation.

In FIG. 8, the aerosol backscattering coefficient profile is depicted, determined by applying the above-described algorithm to the simulated signal, together with that presupposed in the simulation. The continuous curve represents the trend of the backscattering coefficient assumed by hypothesis. The trends obtained in the day and night situations are reported in the Figure.

From the Figure, it is inferred that the backscattering coefficient profile is reconstructed with a deviation lower than 1% for distances from about 200 m to 2 km (lidar-mirror distance). The overall spatial resolution results to be equal to 6 m. The fluctuations which are present for distances lower than 200 m are due to the low intensity of the counterpropagating backscattering signal and to the influence of the overlap function, which takes very low values for very small distances.

Figure 9:
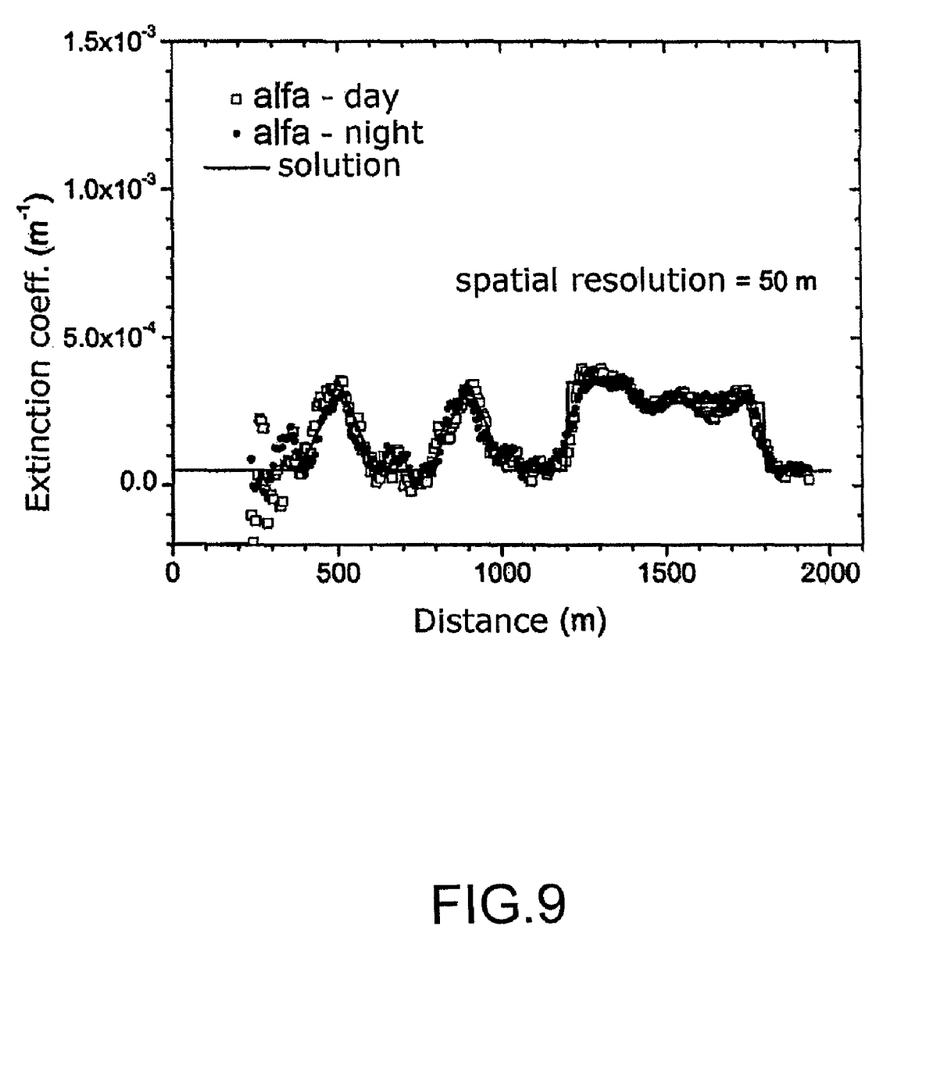
FIG. 9 reports the aerosol extinction coefficient profile determined on the basis of the simulated signal, together with that of the signal assumed by hypothesis in the simulation.

In FIG. 9, the aerosol extinction coefficient profile is depicted, which is determined by applying the above-described algorithm to the simulated signal (day and night), together with that assumed by hypothesis in the simulation.

The preciseness of the reconstruction of the hypothesized profile corresponds to a deviation which is lower than 5% starting from a distance of 400 m. The overall spatial resolution results to be equal to about 50 m.

The simulation of the operation of the complete device demonstrates that the extinction and aerosol backdiffusion coefficients can be determined in an absolute manner, without any hypotheses, with spatial resolutions of the order of a few meters and time resolutions of 10 min, over distances of some kms and with a performance which is practically identical for day and night measurements, using parameters corresponding to real working conditions and commercial components. Furthermore, safety problems [9] when using laser sources are easily solved with those parameters, without thereby decreasing performance.

REFERENCES

[1] Klett, J. D.: Stable analytical inversion solution for processing lidar returns. *Appl. Optics*, 20, 211-220, (1981)

[2] Fernald et al., Determination of Aerosol Height Distributions by Lidar, (1972), *Journal of Applied Meteorology*, 11, pp. 482-489.

[3] Ansmann et al., Combined Raman Elastic Backscatter LIDAR for vertical profiling of moisture, aerosol extinction, backscatter and lidar ratio, (1992) *Appl. Phys. B*, 55, 18-28.

[4] Ansmann et al., Measurement of atmospheric aerosol extinction profiles with a Raman lidar, (1990), *Opt. Lett.* 15, 746-748.

[5] C. Böckmann, Hybrid regularization method for the ill-posed inversion of multiwavelength lidar data to determine aerosol size distribution, *Appl. Opt.*, 40 (2001) 1329-1342.

[6] Müller, D., Wandinger, U., e Ansmann, A. Microphysical particulate parameters from extinction and backscatter lidar data by inversion with regularization: simulation, *Appl. Opt.*, 38(12):2358-2368, (1999).

[7] M. Sicard et al., *Variational method for the retrieval of optical thickness and the backscatter coefficient from multiangle lidar profiles*, (2002), Applied Optics, vol. 41, n. 3.

[8] Wang, Xuan et al.: Retrieval of atmospheric particles optical properties by combining ground-based and space-borne lidar elastic scattering profiles, 28 maggio 2007/Vol. 15, N. 11/OPTICS EXPRESS 6734.

[9] Shane D. Mayor e Scott M. Spuler "Raman-shifted eye-safe aerosol lidar" APPLIED OPTICS Vol. 43, N. 19-1 luglio 2004.

What is claimed is:

1. A method for the characterization of atmospheric particles by means of a lidar device, comprising the following steps:

sending a laser pulse in the atmosphere, a part of which is backscattered by the particles in the atmosphere thus generating a direct backscattering signal that propagates towards the lidar device;

detecting the direct backscattering signal, and determining optical characteristics of the particles on the basis of the detected direct backscattering signal;

wherein it is provided a reflecting optical device that is positioned at a predetermined distance d from the lidar system, whereby a part of the laser pulse that directly reaches the reflecting device is backreflected and is later backscattered by the particles in the atmosphere thus generating a counterpropagating backscattering signal directed towards the reflecting device, which signal reaches the reflecting device and is in turn backreflected by it towards the lidar system, and the counterpropagating backscattering signal is also detected, so that the determination of the characteristics of the particles is made also using the counterpropagating backscattering signal.

2. A method according to claim 1, in which the determination of the characteristics of the particles includes determining the backscattering coefficient of the particles as a function of the distance z from the lidar device and the wavelength $\lambda$ of the laser pulse, on the basis of the product of the detected direct backscattering signal and the detected counterpropagating backscattering signal.

3. A method according to claim 1, in which the determination of the characteristics of the particles includes determining the extinction coefficient of the particles as a function of the distance z from the lidar device and the wavelength $\lambda$, of the laser pulse, on the basis of the ratio between the detected counterpropagating backscattering signal and the detected direct backscattering signal.

4. A method according to claim 1, wherein a further part of the laser pulse directly reaches the reflecting device and is backreflected towards the lidar system without interacting with the particles, thus generating a direct backreflection signal, and wherein the direct backreflection signal is detected separately from said direct and counterpropagating backscattering signals, and is used for calibrating the lidar device.

5. A lidar system for the characterization of atmospheric particles by means of a method according to claim 1, including a lidar device, including a transmitter system for sending said laser pulse in the atmosphere, and a receiver system for detecting said direct and counterpropagating backscattering signals, and a reflecting optical device positioned at a predetermined distance d from the lidar device, and adapted to reflect the part of the laser pulse directly reaching the reflecting device and the counterpropagating backscattering signal towards the lidar device.

6. A lidar system according to claim 5, for the characterization of the atmospheric particles, in which said receiver system of the lidar device includes at least one detector for detecting said direct and counterpropagating backscattering signals, and a different detector for detecting the direct back-reflection signal.

* * * * *